United States Patent
Ueda et al.

(10) Patent No.: US 8,377,015 B2
(45) Date of Patent: Feb. 19, 2013

(54) WOUND DRESSING AND METHOD FOR PRODUCING IT

(75) Inventors: Atsushi Ueda, Tokyo (JP); Toshimichi Matsuzaka, Tokyo (JP)

(73) Assignee: Alcare Co., Ltd., Tokyo (JP)

( * ) Notice: Subject to any disclaimer, the term of this patent is extended or adjusted under 35 U.S.C. 154(b) by 379 days.

(21) Appl. No.: 12/602,340

(22) PCT Filed: Apr. 24, 2009

(86) PCT No.: PCT/JP2009/058190
§ 371 (c)(1),
(2), (4) Date: Apr. 23, 2010

(87) PCT Pub. No.: WO2010/122665
PCT Pub. Date: Oct. 28, 2010

(65) Prior Publication Data
US 2011/0160686 A1    Jun. 30, 2011

(51) Int. Cl.
*A61L 15/56* (2006.01)
*B32B 37/12* (2006.01)

(52) U.S. Cl. ........ 604/304; 604/305; 604/306; 604/307; 604/308; 604/313; 604/356; 604/358; 604/543; 156/60; 156/73.4; 156/329

(58) Field of Classification Search .................. None
See application file for complete search history.

(56) References Cited

U.S. PATENT DOCUMENTS

| | | | | |
|---|---|---|---|---|
| 3,543,750 A | * | 12/1970 | Meizanis | 602/47 |
| 4,341,207 A | * | 7/1982 | Steer et al. | 602/56 |
| 5,098,500 A | * | 3/1992 | Reed et al. | 156/253 |
| 5,328,450 A | * | 7/1994 | Smith et al. | 602/59 |
| 5,409,472 A | * | 4/1995 | Rawlings et al. | 604/307 |
| 5,632,731 A | * | 5/1997 | Patel | 602/59 |
| 5,814,031 A | * | 9/1998 | Mooney et al. | 604/307 |
| 6,566,575 B1 | * | 5/2003 | Stickels et al. | 602/41 |
| 7,429,689 B2 | * | 9/2008 | Chen et al. | 604/378 |
| 2004/0175344 A1 | * | 9/2004 | Woller | 424/70.12 |
| 2007/0202245 A1 | * | 8/2007 | Gantner et al. | 427/2.1 |
| 2007/0299415 A1 | * | 12/2007 | Poccia et al. | 604/367 |
| 2011/0097531 A1 | * | 4/2011 | Godefroidt et al. | 428/41.7 |

* cited by examiner

*Primary Examiner* — Melanie Hand
*Assistant Examiner* — Andrew S Lo
(74) *Attorney, Agent, or Firm* — Young & Thompson

(57) ABSTRACT

To provide a wound dressing having absorbability and improved so as not to be adhere to wounds, a wound dressing 10 is provided, which includes a perforated material 20 having a top face and a bottom face and having plural through-holes 21, and an absorbent material 30 disposed on the top face of the perforated material, and in which at least the bottom face of the perforated material 20 is coated with a silicone resin 40 except leaving at least a part of the through-holes so as not to block up all the through-holes, and at least a part 31 of the absorbent material facing the through-holes of the perforated material is coated with the silicone resin 40, and to allow fluid penetration from the bottom face side of the perforated material into the inside of the absorbent material.

15 Claims, 6 Drawing Sheets

Fig.1
a)
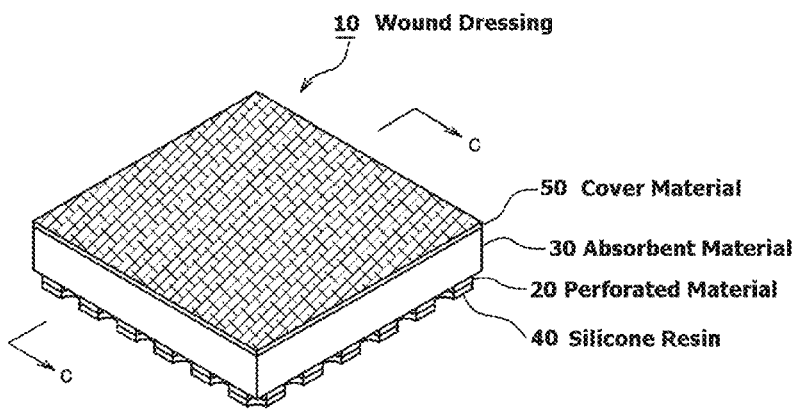
b)
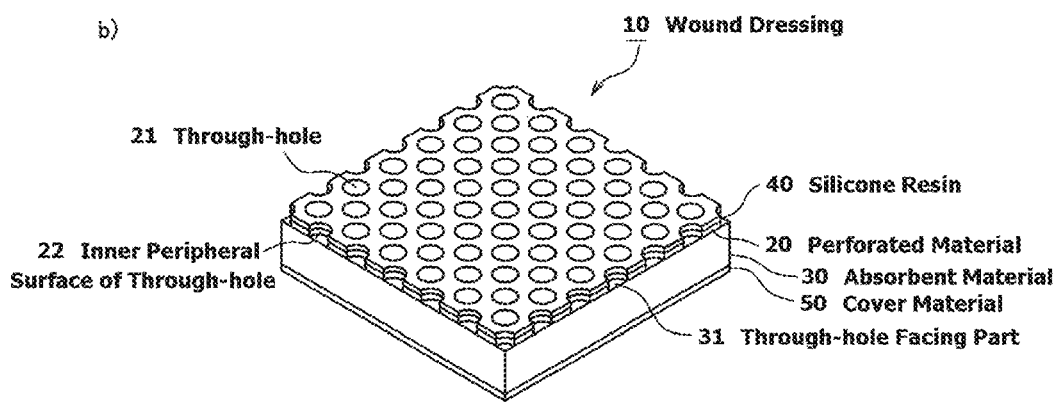
c)
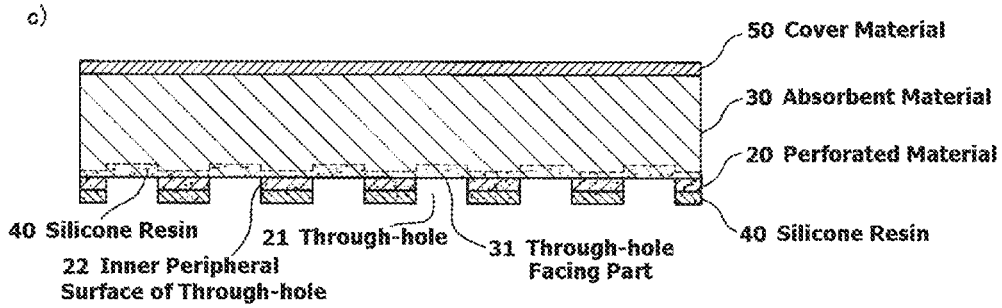

Fig. 3
a)
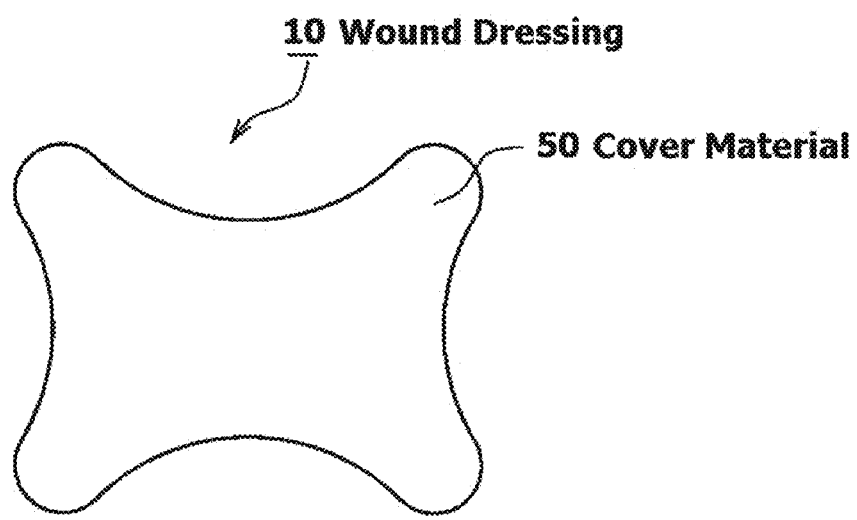
10 Wound Dressing
50 Cover Material
b)
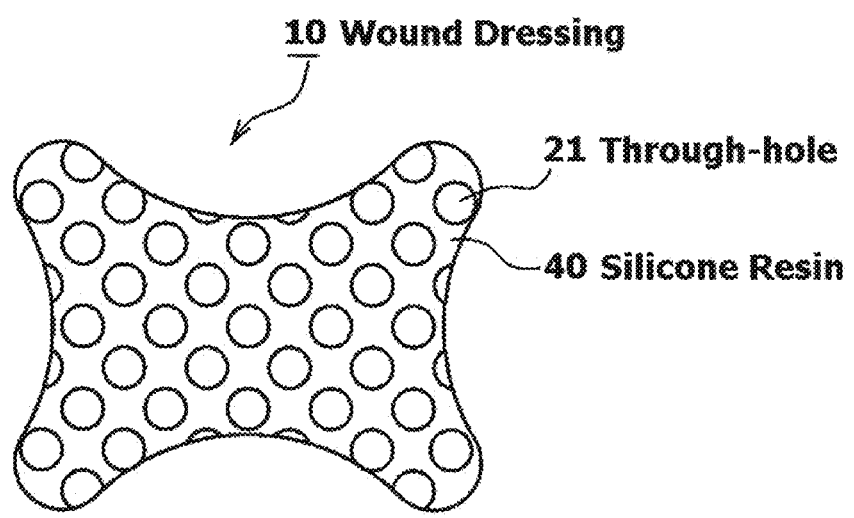
10 Wound Dressing
21 Through-hole
40 Silicone Resin Fig.4
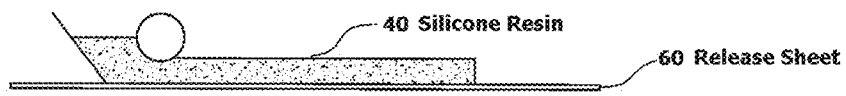
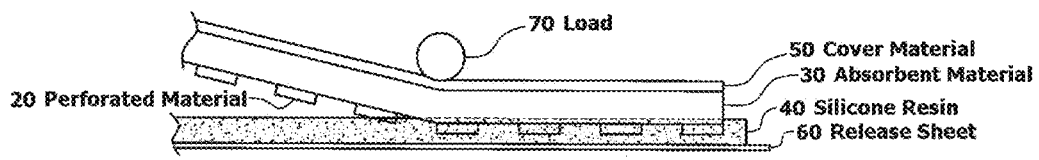
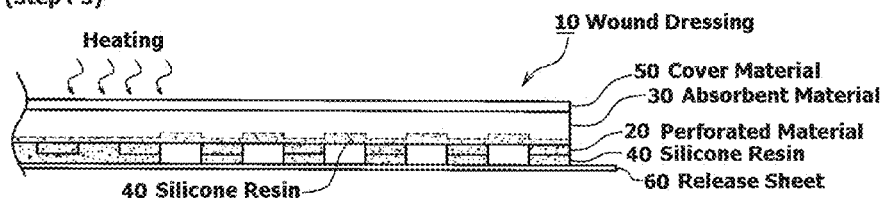
[Fig.5]
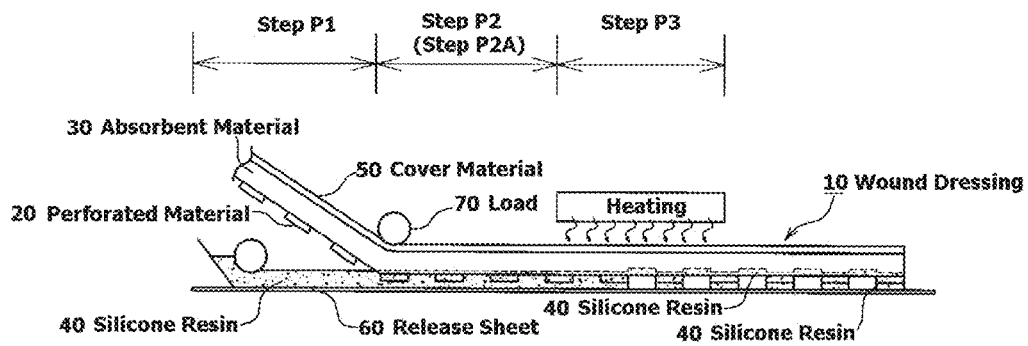

Fig.6
Enlarged Picture of One Through-Hole
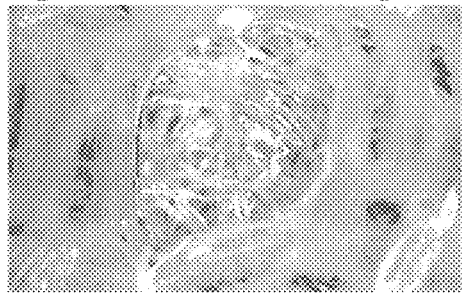
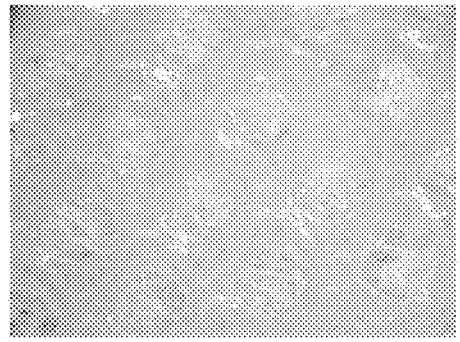
Fig.7
Enlarged Picture of One Through-Hole
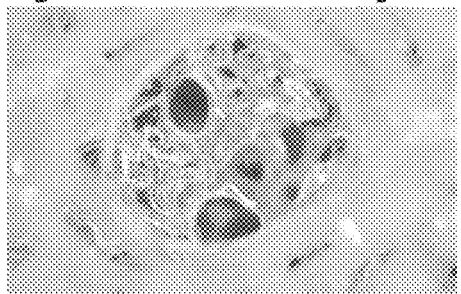
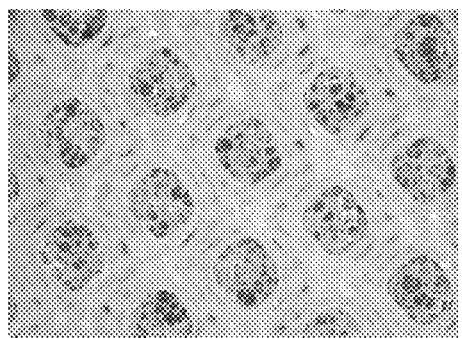
Fig.8
Enlarged Picture of One Through-Hole
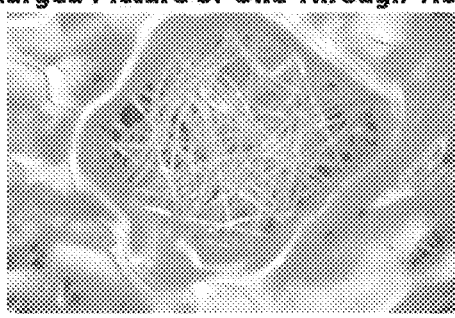
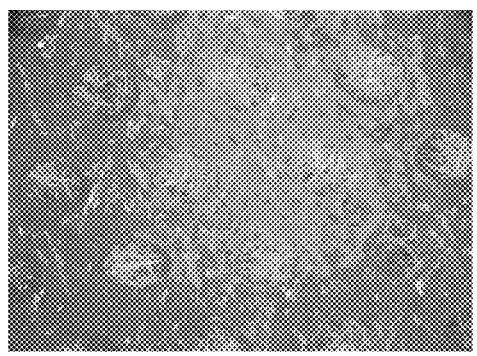
Fig.9
| Comparative Example 1 |||| 
|---|---|---|---|
| On Day 2 || On Day 9 ||
| Look in Peeling | Wound Surface after Peeling | Look in Peeling | Wound Surface after Peeling |

Fig.10
| Example 1 ||||
|---|---|---|---|
| On Day 2 || On Day 9 ||
| Look in Peeling | Wound Surface after Peeling | Look in Peeling | Wound Surface after Peeling |
| 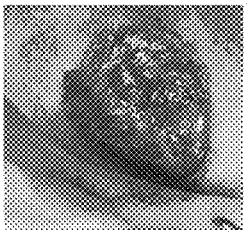 | 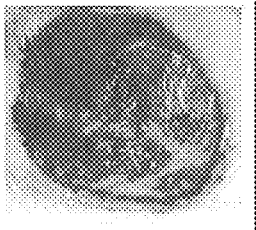 | 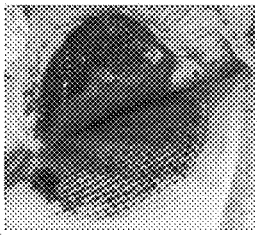 | 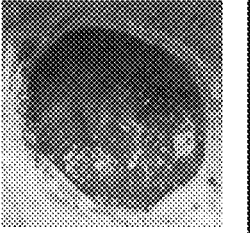 |

WOUND DRESSING AND METHOD FOR PRODUCING IT

TECHNICAL FIELD

The present invention relates to a wound dressing for use for protection and treatment for wounds, and to a method for producing it.

BACKGROUND ART

In treatment for burns, pressure ulcers and other injury, heretofore used are wound dressings such as gauze, cotton, multilayer pads and so on comprising layers of absorbent fibers, for the purpose of protecting the wounds and for absorbing body fluid from the wounds.

However, these wound dressings may damage the wound surface in changing after their application thereto, thereby often causing pain, bleeding and delayed cure of wounds.

On the other hand, wound dressings preferably adhere to the wound area and the wound-surrounding skin for their good handleability for fixation to the area and for the purpose of preventing the wound-surrounding skin from maceration owing to leakage of body fluid.

However, the adhesion of wound dressings comprising a conventional adhesive layer (for example, acrylic adhesive, rubber-base adhesive) tends to be too strong, and therefore they may firmly adhere to the wound area in their exchange and may thereby damage the fragile, neogenetic epidermal tissue to cause delayed cure of the tissue.

Under the background, the material of a wound dressing to be in direct contact with a wound area is preferably one having a low adhesion to body tissues. Especially preferred is a material of a silicone resin having a low affinity for bodies.

Examples of wound dressings comprising an adhesive silicone resin are described. For example, Patent Reference 1 discloses a wound dressing in which a silicon gel seals around all components of a network of an elastic net-like reinforcement but leaving through-holes of the reinforcement. According to the technique of Patent Reference 1, the silicone resin constituting the wound contacting material solves the problem of adherence to wounds.

However, the wound dressing described in Patent Reference 1 has no absorbability, and is therefore troublesome since it must be combined with some absorbent material. In case where an absorbent material is combined with the wound dressing, the absorbent material may be exposed out through the part of the through-holes of the wound dressing. Therefore, the wound dressing involves a risk of easy adhering to the neogenetic tissue of the wound area in that part of the through-holes thereof.

Patent Reference 2 teaches a wound dressing produced by coating one surface of an air-impervious and body fluid-impervious perforated layer material (carrier material) with a silicone gel. This wound dressing comprises an absorbent material and is therefore free from the trouble in Patent Reference 1 where the wound dressing must be combined with an additional absorbent material. However, in the wound dressing described in Patent Reference 2, the applied absorbent material is kept exposed out through the part of the through-holes, like in the wound dressing described in Patent Reference 1, and therefore, Patent Reference 2 could not still solve the problem of easy adhering of the wound dressing to neogenetic tissues.

Patent Reference 1: Japanese Patent 2525215
Patent Reference 2: Japanese Patent 3677283

DISCLOSURE OF THE INVENTION

Problems that the Invention is to Solve

The present invention has been made in consideration of the above-mentioned matters, and the subject matter of the invention is to provide a wound dressing that has absorbability and is free from a trouble of adhering to wounds.

Means for Solving the Problems

For solving the above-mentioned problems, the invention provides a wound dressing that comprises a perforated material having a top face and a bottom face and having plural through-holes, and an absorbent material disposed on the top face of the perforated material, wherein at least the bottom face of the perforated material is coated with a low-adhesive resin except leaving at least a part of the through-holes so as not to block up all the through-holes, and at least a part of the absorbent material facing the through-holes of the perforated material is coated with the low-adhesive resin, and to allow fluid penetration from the bottom face side of the perforated material into the inside of the absorbent material. In the invention, preferably, the top face of the perforated material is coated with the low-adhesive resin except leaving at least a part of the through-holes so as not to block up all the through-holes.

The invention also provides a wound dressing that comprises a perforated material having a top face and a bottom face and having plural through-holes, and an absorbent material disposed on the top face of the perforated material, wherein the top face and the bottom face of the perforated material are coated with a low-adhesive resin except leaving at least a part of the through-holes so as not to block up all the through-holes, at least a part of the absorbent material facing the through-holes of the perforated material is coated with the low-adhesive resin, and the perforated material and the absorbent material are adhered to each other with the low-adhesive resin overlying the top face of the perforated material, and to allow fluid penetration from the bottom face side of the perforated material into the inside of the absorbent material.

Preferred embodiments of the invention are described below. Specifically, the low-adhesive resin is preferably a silicone resin. Also preferably, the low-adhesive resin is an adhesive gel. Preferably, the inner peripheral surface of the through-holes of the perforated material is coated with the low-adhesive resin so as not to block up all the through-holes. Also preferably, the low-adhesive resin penetrates from the bottom face of the perforated material into the inside thereof so as to reach the top face of the perforated material. In one preferred embodiment where the low-adhesive resin is penetrated into the perforated material, the perforated material and the absorbent material are adhered to each other with the low-adhesive resin that penetrates from the bottom face of the perforated material into the inside thereof so as to reach the top of the perforated material. Also preferably, the part of the absorbent material that faces the through-holes of the perforated material is coated with the low-adhesive resin in such a degree that it does not interfere with fluid penetration from the bottom face side of the perforated material into the inside of the absorbent material. Preferably, nearly the entire bottom face of the perforated material is coated with the low-adhesive resin except leaving almost all the through-holes so as not to block up almost all the through-holes, and the part of the absorbent material that faces almost all the through-holes of the perforated material is coated with the low-adhesive resin. Preferably, the amount of the low-adhesive resin to coat the perforated material and the absorbent material is from 150 to 350 g/m$^2$. Preferably, the perforated material is a knitted fabric having a thickness of from 0.05 to 0.7 mm. Preferably, the perforated material has an average through-holes cross section of from 0.01 to 10 mm$^2$ and a perforated rate of from 5 to 70%.

As an invention for a production method for the above-mentioned wound dressing, the following invention is preferred.

Specifically, the invention is a method for producing a wound dressing which comprises a perforated material having a top face and a bottom face and having plural through-holes, and an absorbent material disposed on the top face of the perforated material, and in which at least the bottom face of the perforated material is coated with a low-adhesive resin except leaving at least a part of the through-holes so as not to block up all the through-holes, and at least a part of the absorbent material facing the through-holes of the perforated material is coated with the low-adhesive resin, and to allow fluid penetration from the bottom face side of the perforated material into the inside of the absorbent material, the method comprising the following steps:

(P1) a step of applying a low-adhesive resin to a release sheet, (P2) a step of putting a perforated material on the coated face of the low-adhesive resin before curing and putting an absorbent material on the top face of the perforated material to thereby coat the perforated material and the absorbent material with the low-adhesive resin, (P3) a step of heating and curing the low-adhesive resin.

As the production method of the invention, the following invention is also preferred.

Specifically, the invention is a method for producing a wound dressing which comprises a perforated material having a top face and a bottom face and having plural through-holes, and an absorbent material disposed on the top face of the perforated material, and in which the top face and the bottom face of the perforated material are coated with a low-adhesive resin except leaving at least a part of the through-holes so as not to block up all the through-holes, and at least a part of the absorbent material facing the through-holes of the perforated material is coated with the low-adhesive resin, and the perforated material and the absorbent material are adhered to each other with the low-adhesive resin overlying the top face of the perforated material, and to allow fluid penetration from the bottom face side of the perforated material into the inside of the absorbent material, the method comprising the following steps:

(P1) a step of applying a low-adhesive resin to a release sheet, (P2A) a step of putting a perforated material on the coated face of the low-adhesive resin before curing and putting an absorbent material on the top face of the perforated material, and to make the low-adhesive resin penetrate from the bottom face of the perforated material into the inside thereof so as to reach the top face of the perforated material, whereby the perforated material and the absorbent material are adhered to each other with the low-adhesive resin, and the perforated material and the absorbent material are coated with the low-adhesive resin, (P3) a step of heating and curing the low-adhesive resin.

In one preferred embodiment of the production method of the invention, the low-adhesive resin is a silicone resin.

Advantage of the Invention

In the wound dressing of the invention, both the perforated material and the absorbent material to be in contact with a wound are coated with a low-adhesive resin; and accordingly, even when a neogenetic granulation tissue may invade the wound dressing through the though-holes of the perforated material thereof, the wound dressing can be prevented from firmly adhering to the wound surface, and therefore the wound dressing can be removed and exchanged without damaging the fragile neogenetic epidermal tissue. In addition, since the wound dressing of the invention can rapidly absorb the exudate from a wound into the absorbent material from the wound surface, it may prevent skin maceration and delayed wound cure owing to excessive exudate. Further, according to the production method of the invention, the above-mentioned wound dressing can be produced with ease.

BRIEF DESCRIPTION OF THE DRAWINGS

FIG. 1 It shows a wound dressing of an embodiment of the invention.

FIG. 3 It shows a wound dressing of a still different embodiment of the invention.

FIG. 4 It shows a production method for a wound dressing of the invention.

FIG. 5 It shows a continuous production method for a wound dressing of the invention.

FIG. 6 It shows enlarged views from the perforated material side in Example 1 of the invention.

FIG. 7 It shows enlarged views from the perforated material side in Example 2 of the invention.

FIG. 8 It shows enlarged views from the perforated material side in Comparative Example 1.

FIG. 9 It shows adherence evaluation results in Comparative Example 1.

FIG. 10 It shows adherence evaluation results in Example 1 of the invention.

DESCRIPTION OF REFERENCE NUMERALS

Figure 2:
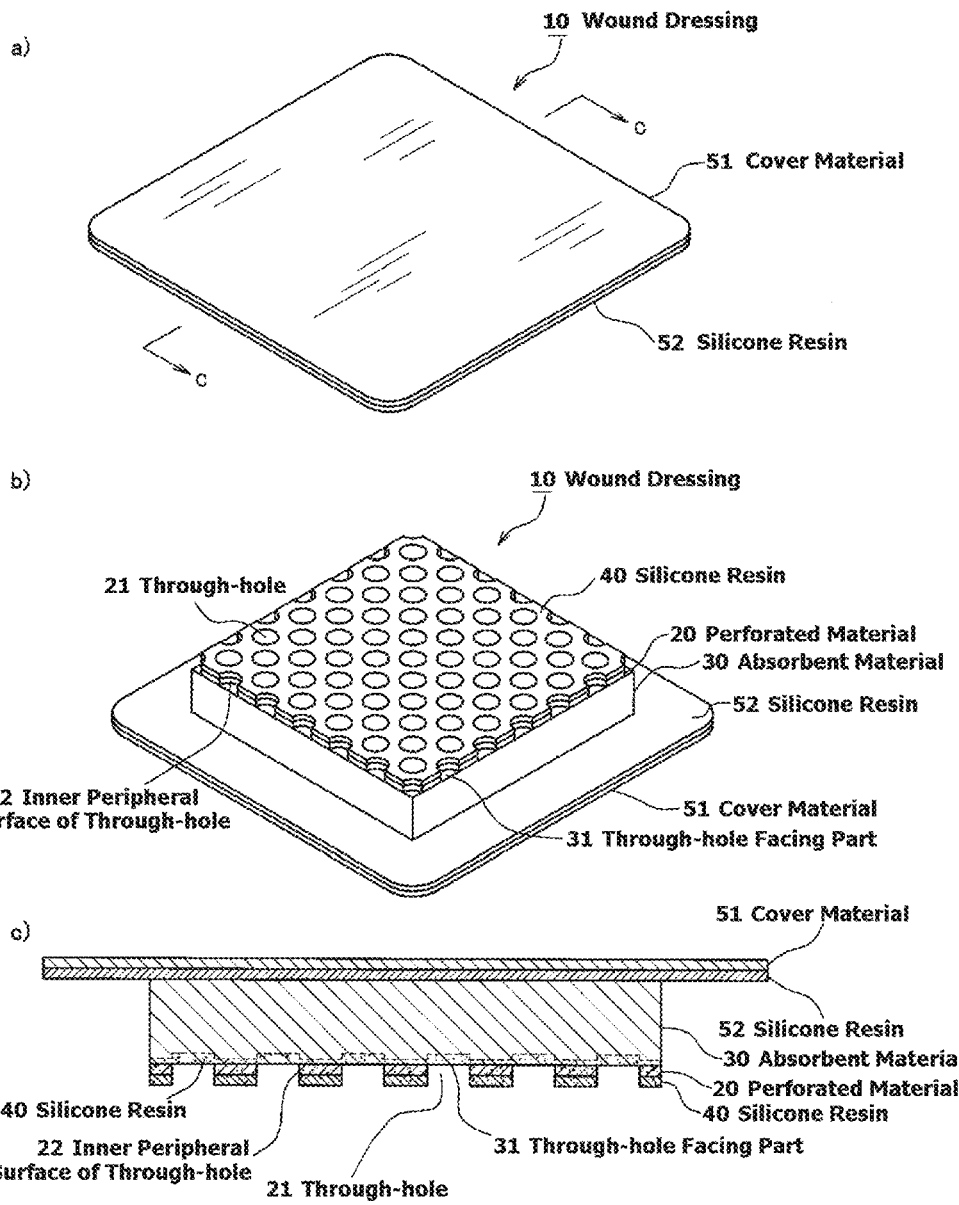
FIG. 2 It shows a wound dressing of a different embodiment of the invention.

10 Wound dressing
20 Perforated material
21 Through-hole
30 Absorbent material
31 Part facing through-hole
40, 52 Silicone resin
50, 51 Cover material
60 Release sheet
70 Load

BEST MODE FOR CARRYING OUT THE INVENTION

With reference to FIGS. 1 to 5, embodiments of the invention are described below. The same reference numeral is given to the common part in these embodiments.

FIG. 1 is an embodiment of a wound dressing of the invention, in which a) is a perspective view from the top face, b) is a perspective view from the bottom face, c) is an enlarged cross-sectional view cut along the C-C line in a).

The wound dressing 10 of the invention comprises a perforated material 20 having a top face and a bottom face, and an absorbent material 30 disposed on the top face of the perforated material 20. The perforated material 20 is formed of a knitted fabric, its knit structure forms plural through-holes 21 therein, and its bottom side is to face a wound.

The top face and the bottom face of the perforated material 20 and the inner peripheral surface 22 of each through-hole 21 are coated with a gel-like adhesive silicone resin 40 except leaving at least a part of the through-holes (in this embodiment, leaving all the through-holes) so as not to block up all the through-holes 21. Specifically, the wound dressing 10 of the invention is so designed that the silicone resin 40 coats the perforated material 20 except leaving at least a part of the through-holes (in this embodiment, all the through-holes) running from the top face to the bottom face of the perforated material 20 to thereby let a fluid such as blood or exudate pass from the bottom side of the perforated material into the inside of the absorbent material 30. As described below, in general, a release sheet (not shown) is provided on the bottom face side of the silicon resin 40, as a protective material for the silicon resin-coating layer and the perforated material before use of the wound dressing.

Of the absorbent material 30, the part 31 that faces the through-hole 21 of the perforated material 20 is partly coated with the gel-like adhesive silicone resin in such a degree that it does not interfere with passing of a fluid such as blood or exudate from the bottom face side of the perforated material to the inside of the absorbent material. For example, in case where a nonwoven fabric is used as the absorbent material 30, as described below, a part of the nonwoven fabric is coated with a silicone resin in such a manner that the silicone resin may cling and adhere to a part of the nonwoven fabric while the silicone resin does not adhere to the other part thereof to allow fluid penetration therethrough.

As in the embodiment in FIG. 1, the entire surface of the perforated material 20, or that is, the top face and the bottom face of the perforated material 20 and the inner peripheral face of each through-hole are coated with the silicone resin 40, and further the part 31 of the absorbent material 30 that faces the through-hole 21 of the perforated material 20 is partly coated with the silicone resin 40, whereby even when a neogenetic granulation tissue being in cure invades the through-holes of the perforated material, the wound dressing can maintain good non-adhesiveness to the wound and, in addition, the wound dressing can rapidly absorb the exudate from the wound, from the wounded skin surface into the absorbent material thereof.

In the embodiment in FIG. 1, in addition, the gel-like adhesive silicone resin 40 penetrates into the inside of the knitted fabric from the bottom face of the perforated material 20 to reach the top face of the perforated material. And the perforated material 20 and the absorbent material 30 are adhered to each other with the silicone resin 40 existing in the top face of the perforated material. In that manner, in the wound dressing 10 of the embodiment in FIG. 1, one type of the adhesive silicone resin 40 acts to coat the perforated material and the absorbent material and acts to integrate the perforated material and the absorbent material, and therefore, the material constitution is simple and the production process is extremely simple.

50 is a cover material to cover the top face of the absorbent material 30, and it functions to protect the absorbent material from being contaminated, to support the wound dressing and to prevent a contaminant from removing from the absorbent material. In the embodiment in FIG. 1, a liquid-pervious nonwoven fabric is used as the cover material 50, and the cover material is an especially advantageous constitution in a case where much exudate bleeds from a wound. In other words, since excessive exudate may bleed out through the cover material, another absorbent pad apart from the wound dressing of the invention may be put on the cover material, whereby only this absorbent pad may be exchanged, if desired, not removing the wound dressing of the invention, and this simplifies the exudate treatment. In addition, in case where the cover material is a liquid-pervious one in that manner, the wound dressing of the invention is useful as a pad in negative pressure wound therapy or in a wound irrigation system. Concretely, the wound dressing of the invention may be used in the following method. First, the wound dressing of the invention is put on a wound, then a tube is put on the cover material of the wound dressing, and a fluid suction source like a pump and/or a washing liquid bag or the like is connected to the tube. With that, over the tube, the wound area is entirely covered with a liquid-impervious adhesive film or bag so that the wound dressing could be in a sealed condition. Then, the exudate from the wound is drained or the wound is irrigated through suction and/or liquid introduction via the tube, whereby the wound cure may be promoted. The wound dressing of the invention has good fluid permeability, and when it is removed, it gives little peeling irritation; and therefore, as combined with the therapeutical method, the wound dressing enables simple and effective wound treatment.

In the embodiment of FIG. 1, the adhesive silicone resin is applied to the entire surface of the perforated material (top face, bottom face and inner peripheral surface of through-holes); however, the embodiment may be modified to an embodiment where only the bottom face of the perforated material is coated, or to an embodiment where only the bottom face and the top face of the perforated material are coated.

Preferably, the perforated material 20 is so coated with the silicone resin that all the through-holes 21 are not blocked up with the silicone resin; however, a part of the through-holes 21 may be blocked up with the silicone resin not interfering with liquid penetration into the inside of the absorbent material.

The perforated material 20 and the absorbent material 30 may be adhered to each other with an adhesive except silicone resin, such as an acrylic adhesive, a rubber-base adhesive or a polyurethane adhesive, or they may be adhered by heat-sealing.

FIG. 2 shows an embodiment of a wound dressing of the invention, different from that in FIG. 1; and a) is a perspective view from the top face, b) is a perspective view from the bottom face, and c) is an enlarged cross-sectional view cut along the C-C line in a).

The embodiment in FIG. 2 differs from the embodiment in FIG. 1 in point of the cover material 51. Specifically, the cover material 51 comprises a liquid-impervious but water vapor-pervious plastic film, and is coated with an adhesive silicone resin 52 on its bottom face, and its outer peripheral edge extends outside over the outer peripheral edge of the absorbent material 30. When the wound dressing is fixed on a wound area, then the part extending outside may cover the components below the absorbent material.

Therefore, according to the embodiment in FIG. 2, the wound dressing can be fixed to a wound area by the cover material 51 in a simplified manner; and even when the exudate is excessive, the exudate may be prevented from bleeding out from the outer peripheral edge of the absorbent material and the wound may be kept in a suitable moist environment to thereby promote wound cure.

FIG. 3 is an embodiment of which the shape is modified from that of the wound dressing in FIG. 1 of the invention. In this embodiment, even when applied to a projected part or a curved part such as heel, elbow, knee, sacral spine or forearm, the wound dressing of this embodiment may well fit to the wound area and may be applied thereto with no wrinkle.

The shape of the wound dressing of the invention is not limited to those of the above-mentioned embodiments, but various shapes easy to fit to the shapes of various parts of human bodies are employable. The wound dressing may be in a clothing form for covering or wrapping a wound area. Preferred examples of the wound dressing in a clothing form of the invention include sleeve-like or belt-like clothing to cover extremities, trunk (thoracic region, abdomen, etc.), neck, head, etc.; upper-body clothing such as shirt-like clothing (sleeved or sleeveless shirts, etc.); lower-body clothing such as socks-like, knee-length socks-like, stockings-like, tights-like or shorts-like clothing, etc. Especially preferred are sleeved or lower-body clothing forms; and these are effective for treatment for ulcer or foot amputation accompanied by diabetic foot disease or peripheral arterial disease (PAD). In case where the wound dressing is processed to have such a clothing form, the wound dressing may be so designed that the perforated material coated with a low-adhesive resin is disposed on the inner face side of the clothing that is to be in contact with a skin, for which are suitably employable any known sewing, knitting, weaving techniques, etc.

In the embodiments shown in the above-mentioned FIGS. 1 to 3, a silicone resin is used as the low-adhesive resin to cover the perforated material and the absorbent material; however, any other low-adhesive resin than silicone resin is also employable.

Next, methods for producing the wound dressing of the invention are described with reference to FIG. 4 and FIG. 5.

The wound dressing of the invention is produced in a process of steps P1, P2 (P2A) and P3 in that order. FIG. 5 is a view schematically showing a continuous process of the above-mentioned steps, in which each step is substantially the same as in FIG. 4.

The step of P1 is a step of applying a silicone resin 40 to a release sheet 60. As the release sheet, usable is release paper or a release film processed with a silicone series or fluorine series release agent; a film of polycarbonate, polyvinyl alcohol, cellophane, urethane or the like.

In the step of P2, a perforated material 20 is put on the silicone resin-coated face 40 before curing, and further an absorbent material 30 (the absorbent material may be previously laminated with a cover material 50 on the top face thereof) is put on the top face of the perforated material 20. In this step, the silicone resin, the perforated material and the absorbent material may be laminated nearly at the same time as in FIG. 4 and FIG. 5; but the perforated material may be first supplied onto the silicone resin and thereafter the absorbent material may be supplied thereon. In that manner, the perforated material is put on the silicone resin, and the absorbent material is further put thereon, whereby the perforated material except the part of through-holes, and the part of the absorbent material that faces the through-holes of the perforated material are coated with the silicone resin.

The step of P2 is especially preferably the step of P2A mentioned below. In the step of P2A, a perforated material 20 is first put on the silicone resin-coated face 40 before curing, and an absorbent material 30 is put on the top face of the perforated material 20, like in the step of P2. Next, a suitable load 70 is given to the laminate to thereby make the silicone resin 40 penetrate from the bottom face of the perforated material 20 into the inside thereof so as to reach the top face of the perforated material, whereby the perforated material 20 and the absorbent material 30 are adhered to each other with the silicone resin 40. Simultaneously with the adhesion of the perforated material 20 and the absorbent material 30, the silicone resin existing in the part of the through-holes of the perforated material is absorbed by the surface of the absorbent material to thereby coat the part of the absorbent material facing the through-holes of the perforated material with the silicone resin. Specifically, in the step of P2A, the perforated material is coated with the silicone resin not blocking up the through-holes of the perforated material, and the absorbent material is also coated with the silicone resin, and further, the perforated material and the absorbent material are adhered to each other simultaneously in one step.

The step of P3 is a step of heating and curing the silicone resin applied to the perforated material and the absorbent material in the step of P2 (P2A); and the uncured liquid silicone resin is cured in this step to complete the wound dressing 10 of the invention.

Wound dressings of various types of embodiments of the invention can be produced by controlling the type and the coating amount of the silicone resin, the type of the perforated material and the absorbent material, the degree of the load, etc.

The wound dressing of the invention can be produced in any other method than the above, for which, for example, there may be mentioned a method comprising dipping a perforated material in an uncured silicone resin, removing the excessive silicone resin by squeezing, then putting an absorbent material thereon, heating and curing the silicone resin, and thereafter applying a silicone resin by spraying or the like to thereby coat the part of the absorbent material that faces the through-holes of the perforated material with the silicone resin.

In the embodiments of the production method of the invention shown in FIGS. 4 and 5, a silicone resin is used as the low-adhesive resin to cover the perforated material and the absorbent material; however, any other low-adhesive resin than silicone resin is also usable in the same method.

Various materials and others constituting the wound dressing of the invention are described below.

(Perforated Material)

The perforated material for use in the wound dressing of the invention has a top face and a bottom face, and it faces a wound on the bottom face side thereof. The perforated material must have plural through-holes running through it from the top face to the bottom face thereof. This is for the purpose of making the blood, the exudate and the like from a wound absorbed by the absorbent material via the through-holes of the perforated material.

The average cross section of the through-holes to be provided in the perforated material is preferably from 0.01 to 10 $mm^2$/hole in the surface of the perforated material, more preferably from 0.1 to 5 $mm^2$/hole. In case where the average cross section of the through-holes is smaller than 0.01 $mm^2$, then the silicone resin may block up the through-holes of the perforated material when the perforated material is coated with a silicone resin, thereby bringing about a risk of no movement of exudate from the perforated material to the absorbent material. When the average cross section of the through-holes is larger than 10 $mm^2$, then the perforated material could not secure a sufficient contact area with a wound surface, thereby bringing about a risk of poor adhesiveness of the wound dressing to the wound to cause exudate leakage.

Preferably, the perforated material in the invention has a perforated rate of through-holes of from 5 to 70%, more preferably from 15 to 50%. When the perforated rate of through-holes is smaller than 5%, then there may be a risk of no movement of exudate from the perforated material to the absorbent material; but when the perforated rate is larger than 70%, then the perforated material could not secure a sufficient contact area with a wound surface, thereby bringing about a risk of poor adhesiveness of the wound dressing to the wound to cause exudate leakage.

Especially preferably, the perforated material has an average cross section of through-holes of from 0.1 to 1 mm$^2$ and a perforated rate of through-holes of from 15 to 40%.

Also preferably, the thickness of the perforated material is within a range of from 0.05 to 0.7 mm from the viewpoint of the movability of exudate to the absorbent material and the non-adhesiveness of the wound dressing to a wound surface.

Not specifically defined, the perforated material usable in the invention may be any sheet material having through-holes, including fibrous materials such as knitted fabric, woven fabric, nonwoven fabric, net; perforated plastic films, etc. Preferably, the perforated material is a liquid-pervious fibrous material, more preferably a knitted fabric that may be readily processed for formation of through-holes therein and is most suitable for the production methods of the wound dressing of the invention.

For the perforated material, one type of these materials may be used singly, or the same or different types of materials may be laminated to give a laminate structure.

As the knitted fabric for the perforated material, usable are various knitted textures of warp knits and weft knits. Especially preferred knitted fabrics are plain-knitted fabrics, rib-stitch fabrics, tricot fabrics, raschel fabrics. The woven fabric may be any of plain-weave fabrics, twill-weave fabrics and sateen-weave fabrics. For the nonwoven fabric, employable is any of a dry method, a wet method and a spun-bonding method for fleece formation; and in the nonwoven fabric, the fiber bonding may be formed in any method of a spun-lace method, a needle-punching method, a chemical bonding method, a point sealing method, a thermal bonding method or the like.

As the net, usable is one produced by disposing plural long fibers at suitable intervals so as to form a network structure followed by bonding the fibers according to a bonding means of thermal fusion or with an adhesive or the like.

The yarns constituting the fibrous materials of knitted fabrics, woven fabrics, nonwoven fabrics, nets and others may be any of monofilaments, multifilaments, twisted yarns, covered yarns, core yarns, etc.; and those processed for shrinkability or for bulkiness are also usable.

The type of the fibers is not also specifically defined, for which, for example, usable are polyester fibers, acrylic fibers, polyamide fibers, polyurethane fibers, cellulose fibers (cotton, rayon, polynosic, lyocell), polyolefin fibers, polyvinyl chloride fibers, polyvinylidene chloride fibers, glass fibers, carbon fibers, etc.

Especially preferred fibrous materials are thermoplastic polyester fibers, acrylic fibers and polyamide fibers.

The disposition of through-holes in the perforated material is not specifically defined, and the through-holes may be disposed regularly or randomly, or may be disposed to form a predetermined pattern such as a lattice-like, wave-like, concentric or whorl-like pattern. Preferably, the through-holes are disposed at uniform intervals so as to secure uniform exudate penetration through the perforated material as a whole.

The through-holes of the perforated material may be those that a fibrous material naturally has, for example, the through-holes of knitted loops of a knitted fabric, the through-holes to form in the surface of a fabric owing to the balance of the fiber texture (including the thickness and density of yarn), and the voids to form between the warp and the weft of a woven fabric; or may also be those physically perforated in post-processing of a material.

Of those, preferred are the through-holes of loops of a knitted fabric or the through-holes to form in the surface of a fabric owing to the balance of the knitted texture (including the thickness and the density of yarn), since the fibrous material of the type is well fittable to human bodies by itself, and since the through-holes are hardly blocked up when coated with a silicone resin layer.

(Absorbent Material)

The absorbent material for use in the wound dressing of the invention is one for absorbing the blood and the exudate from a wound and holding them therein; and this is disposed on the top face of the perforated material.

For the absorbent material, usable are a fibrous material such as nonwoven fabric, knitted fabric, woven fabric; a foam material, an absorbing resin material, a water-absorbing powdery material, etc. Preferred are a fibrous material and a foam material. For the absorbent material, one type of these materials may be used singly, or the same or different types of materials may be laminated to give a laminate structure.

Especially preferred are those of a fibrous material; and preferred fibrous materials are cellulose fibers (cotton, rayon, polynosic, lyocell), polyester fibers, acrylic fibers, polyamide fibers, polyurethane fibers, or their mixed fibers. A material having high water absorbability such as an absorbing resin material or a water-absorbing powdery material may be mixed in these fibrous materials to thereby suitably control the necessary absorption level.

Preferably, a substance capable of forming a gel in absorbing water may be mixed in the material to constitute the absorbent material. Using the material of the type may keep a wound in a moist condition and may promote wound cure. As the gel-forming material, preferred are sodium carboxymethyl cellulose, crosslinked product of sodium carboxymethyl cellulose, starch-acrylic acid (salt) graft copolymer, acrylic acid (salt) polymer, starch-acrylonitrile copolymer, polyalcohol, etc.

(Low-Adhesive Resin)

Not specifically defined, the low-adhesive resin for use in the wound dressing of the invention may be any one having adhesiveness to such a degree that, when the wound dressing of the invention is applied to a wound area and is removed from it, then it does not much irritate or damage the skin and the wound. The low-adhesive resin in the invention includes natural and synthetic polymer substances and mixtures of plural such substances, as well as those prepared by adding any other substance to those polymer substances. The low-adhesive resin for use in the invention may be hydrophilic or hydrophobic, and may be used in the form of an organogel or a hydrogel as combined with a suitable liquid substance. Also usable is a form of a hydrocolloid, as blended with a hydrophilic polymer compound. Especially preferably, the low-adhesive resin is a hydrophobic resin, and also preferably, it is used as a form of a hydrophobic gel. As the material of the hydrophobic resin, such one may be selected that the contact angle between the surface of the layer formed of the resin and water could be at least 65°, and for example, it includes silicone resin, acrylic resin, methacrylic resin, polyvinyl chloride resin, polyvinylidene chloride resin, fluororesin, olefinic resin, polyester resin, styrene resin, urethane resin, polyamide resin, and their mixtures. In particular, preferred are materials containing a silicone resin. The contact angle may be measured with a contact angle meter, CA-A (by Kyowa Interface Science) in accordance with the instruction manual for the contact angle meter "measurement operation for a liquid droplet method".

(Silicone Resin)

The silicone resin favorable for the low-adhesive resin for use in the wound dressing of the invention is applied to at least the bottom face of the perforated material and the part of the absorbent material facing the through-holes of the perforated material, for the purpose of reducing the adhesiveness of the wound dressing to wounds.

The silicone resin for use in the invention is preferably an adhesive gel substance from the viewpoint of the simplicity in handling it and the non-adhesiveness thereof to wounds.

Not specifically defined, the silicone resin may be any one type of addition reaction, peroxide reaction or condensation; but preferred is an addition reaction-type silicone resin.

The addition reaction-type silicone resin is one produced through addition reaction (hydrosilylation reaction) of an organo polysiloxane having an alkenyl group bonding to a silicon atom (alkenyl group-having organo polysiloxane) and an organo polysiloxane having a hydrosilyl group (Si—H) (hydrogen-organo polysiloxane) by the use of a platinum compound catalyst such as chloroplatinic acid.

In the addition reaction-type silicone resin, the crosslinking density may be controlled by changing the amount of the organo hydrogen polysiloxane to be used and the amount of the hydrosilyl group (Si—H) in the organo hydrogen polysiloxane molecule. Accordingly, the hardness and the adhesion of the silicone resin may be readily controlled. The addition reaction-type silicone resin for use in the invention is preferably an addition reaction product of a vinyl group-substituted polydimethylsiloxane and an organo hydrogen polysiloxane.

One or more different types of silicone resins may be used either singly or as combined. Preferably, the silicone resin is cured through crosslinking or the like. The curing method for the silicone resin is not specifically defined. For example, the resin may be readily crosslinked by heating or the like.

The silicone resin may suitably contain any of other chemicals, water-absorbing polymer compounds, pH controlling agents and other controlling agents, not detracting from the object of the invention. Examples of the chemicals include substances of regulating the physiological function of skin for the purpose of moisturization, antiaging, whitening, etc.; as well as substances for promoting wound cure, antimicrobial substances, etc. Their specific examples include sphingolipids, ureas, glycolic acids, amino acids and their derivatives (arginine, cysteine, glycine, lysine, proline, serine, etc.), protein hydrolysates (collagen, elastin, keratin, etc.), mucopolysaccharides and their derivatives (hyaluronic acid, chondroitin sulfate, heparin, etc.), vitamin B groups (thiamine, riboflavin, nicotinic acid, pyridoxine, pyridoxal, pyridoxamine, biotin, folic acid, cyanocobalamin, etc.), ascorbic acids (vitamin C and its derivatives), retinoids (vitamin A, retinal, retinoic acid, etc.), vitamin D (D2, D3, etc.), vitamin E and its derivatives, carotenoids (carotene, lycopene, xanthophyll, etc.), enzymes, coenzymes, γ-orizanol, etc. Especially preferred are sphingolipids. As the sphingolipids, preferred are ceramides of sphingosine and fatty acid bonding thereto, and sphingoglycolipids of ceramide and saccharide bonding thereto. The ceramides may be any of natural or synthetic ones, including Type 1 to Type 7 ceramides. Especially preferred are Type 2, 5 and 7 ceramides. The sphingoglycolipids are preferably cerebroside, galactosyl ceramide, glucosyl ceramide, etc.

The water-absorbing polymer compounds and the pH controlling agents for use herein may be any known ones.

(Cover Material)

Preferably, the wound dressing of the invention is covered with a cover material on the top face of the absorbent material thereof, from the viewpoint of protecting the absorbent material from contamination, securing the handleability of the wound dressing, and preventing a contaminant from removing from the absorbent material.

The cover material may be selected in accordance with the amount of the exudate from a wound and with the site to which the wound dressing is applied. In case where the amount of exudate is large, preferably used is a liquid-pervious material; but in case where the amount is not so large, preferably used is a liquid-impervious but water vapor-pervious material.

The cover material may be coated with an adhesive on the bottom face thereof and its external form may be made larger than that of the perforated material and the absorbent material, whereby the wound dressing of the type may be adhered and fixed to a wound area at the part of the cover material extending outward from the outer peripheral edge of the perforated material and the absorbent material.

The adhesive to coat the bottom face of the cover material may be the same as the silicone resin to coat the perforated material and the absorbent material, but may be any other adhesive than silicone resin, such as acrylic adhesive, rubber-base adhesive or water-absorbing polymer-containing hydrocolloid adhesive.

The cover material includes fibrous sheets such as non-woven fabric, knitted fabric, woven fabric, net; synthetic resin films, foams, etc. The degree of liquid permeability of the cover material may be controlled by suitably selecting any of those materials.

(Coating of Perforated Material and Absorbent Material with Low-Adhesive Resin)

In the wound dressing of the invention, at least the bottom face of the perforated material is coated with a low-adhesive resin except leaving a part of the through-holes thereof so as not to block up all the through-holes. A part of the through-holes of the perforated material may be blocked up with the low-adhesive resin so far as a fluid can run into the inside of the absorbent material from the bottom face side of the perforated material; however, at least 60% of the through-holes remain as such, not blocked up with the low-adhesive resin, more preferably at least 80% of the through-holes remain as such, even more preferably almost all the through-holes remain as such not blocked up with the low-adhesive resin. In particular, it is desirable that almost the entire bottom face of the perforated material is coated with the low-adhesive resin except leaving almost all the through-holes therein so as not to block up almost all the through-holes of the perforated material. Since the through-holes of the perforated material are not blocked up with the low-adhesive resin, exudate may run into the inside of the absorbent material from the bottom face side of the perforated material.

Preferably, the top face of the perforated material is also coated with the low-adhesive resin to reduce the adhesiveness of the wound dressing to wounds; and more preferably, the entire surface of the perforated material including the inner peripheral surface of the through-holes is coated with the low-adhesive resin.

In the wound dressing of the invention, the part of the absorbent material that faces the through-holes of the perforated material is at least partly coated with the low-adhesive resin. However, even though the absorbent material is coated with the low-adhesive resin, a fluid such as blood and exudate must be able to run into the inside of the absorbent material from the bottom face side of the perforated material. For enabling the fluid passage, preferably, the part of the absorbent material that faces the through-holes of the perforated material is coated with the low-adhesive resin to such a degree that the coating does not interfere with the fluid passage.

Preferably, the absorbent material is coated with the low-adhesive resin in the part thereof that faces at least 60% of the through-holes of the perforated material, more preferably, in the part thereof that faces at least 80% of the through-holes of the perforated material; and even more preferably, the part thereof that faces almost all the through-holes of the perforated material is coated with the low-adhesive resin. The absorbent material coated with the low-adhesive resin in the ratio as above may prevent local adhering of the wound dressing to wounds, may prevent tissue damage, and may reduce peeling irritation as a whole of the wound-contact face thereof.

The amount of the low-adhesive resin to coat the absorbent material is preferably from 5 to 150 g/m$^2$, more preferably from 15 to 100 g/m$^2$. When the amount of the low-adhesive resin to coat the absorbent material is smaller than 5 g/m$^2$, then it may be difficult to prevent the absorbent material from adhering to wounds; but when the amount is larger than 150 g/m$^2$, then the low-adhesive resin may block up the void part of the absorbent material thereby bringing about a possibility that the absorbent material could not efficiently absorb exudate.

Also preferably, the perforated material and the absorbent material are adhered to each other with the low-adhesive resin overlying the top face of the perforated material, from the viewpoint of the non-adhesiveness of the wound dressing to wounds and the productivity thereof. As the embodiment of adhering the perforated material and the absorbent material to each other with the low-adhesive resin, preferred is an embodiment where the low-adhesive resin is made to penetrate from the bottom face of the perforated material into the inside thereof so as to reach the top face of the perforated material, whereby the two are adhered to each other with the low-adhesive resin. The embodiment is advantageous in point of the productivity of the wound dressing since the perforated material is coated with the low-adhesive resin and simultaneously the perforated material is integrated with the absorbent material.

The amount of the low-adhesive resin to be applied to the whole of the wound dressing including both the perforated material and the absorbent material is preferably from 150 to 350 g/m$^2$, more preferably from 170 to 250 g/m$^2$. When the amount is smaller than 150 g/m$^2$, then it may be difficult to prevent the wound dressing from adhering to wounds, and it may also be difficult to make the low-adhesive resin penetrate into the inside of the perforated material and to adhere the perforated material to the absorbent material. On the other hand, when the amount is larger than 350 g/m$^2$, then there may be a possibility that the low-adhesive resin may block up the through-holes of the perforated material and the void part of the absorbent material whereby the absorbent material could not efficiently absorb exudate.

Preferably, the adhesion of the wound dressing of the invention is from 0.1 to 1.5 N/25 mm, more preferably from 0.15 to 1.2 N/25 mm. When the adhesion of the wound dressing is smaller than 0.1 N/25 mm, then the wound dressing could not well adhere to a wound area; but when larger than 1.5 N/25 mm, then the wound dressing may damage the wound surface in changing after its application thereto. In case where an adhesive cover is provided, as extending from the outer peripheral edge of the absorbent material, like in the embodiment of FIG. 2 described in the above, the low-adhesive resin for use in the wound dressing of the invention may be so designed that it may exhibit little adhesiveness.

EXAMPLES

The invention is described in more detail with reference to the following Examples, to which, however, the invention should not be limited.

The properties of the wound dressing of the invention were measured according to the methods mentioned below.
[Average Through-Holes Cross Section of Perforated Material (Unit: mm$^2$)]

The bottom face of a perforated material is observed with a microscope in the perpendicular direction thereto (in the direction perpendicular to the bottom face), and the cross section of five through-holes is measured individually. The data are averaged.
[Perforated Rate of Perforated Material (Unit: %)]

The bottom face of a perforated material is observed with a microscope in the perpendicular direction thereto (in the direction perpendicular to the bottom face), and the number of pores in a predetermined area is counted. The perforated rate is derived from the found data, based on the average cross section computed in the above.
[Thickness of Perforated Material (Unit: mm)]

According to JIS L 1096 "Ordinary Woven Fabric Test Method", the thickness of the perforated material before coated with a low-adhesive resin is measured.
[Adhesion of Wound Dressing (Unit: N/25 mm)]

Measured according to JIS Z 0237-2000 "180-degree peeling adhesion force". A Bakelite plate is used as the object to which the test piece is adhered.
[Amount of Low-Adhesive Resin Applied to Absorbent Material (g/m$^2$)]

Before producing a wound dressing, the weight of the absorbent material not as yet coated with a low-adhesive resin is previously measured (W1). After a wound dressing is produced, the absorbent material is separated from the perforated material, and its weight is again measured (W2). From the weight change between W1 and W2, the amount of the low-adhesive resin applied to the absorbent material per unit area (g/m$^2$) is computed.

Example 1

A wound dressing was produced according to the production method comprising the steps P1, P2A and P3 described in FIG. 4. Concretely, this is as follows:

A two-pack addition-reactive silicone resin (Dow Corning's trade name, "DOW CORNING 7-9800") mainly comprising a vinyl group-substituted polydimethylsiloxane, a organo hydrogen polysiloxane and a platinum catalyst was mixed, and the resulting mixture was applied onto a silicone release sheet to form thereon a coating layer having a predetermined thickness. Next, a perforated material of a polyester tricot, and an absorbent material of a nonwoven fabric containing rayon fibers and others were applied onto the silicone resin coating layer. Then, a predetermined load was given to the laminate comprising the silicone resin, the perforated material and the absorbent material, whereby the perforated material and the absorbent material were coated with the silicone resin and the perforated material and the absorbent material were adhered to each other with the silicone resin. Next, this was heated at 110° C. for 2 minutes to cure the silicone resin, thereby giving a wound dressing of the invention. FIG. 6 shows an enlarged view of the thus-obtained wound dressing, taken from the perforated material side thereof. As in FIG. 6, it is known that the silicone resin clung and adhered to a part of the nonwoven fabric of the absorbent material, but did not adhere to the remaining part thereof, and therefore the absorbent material was kept pervious to fluid.

Example 2

A wound dressing was produced according to the same method as in Example 1, for which, however, a polyurethane foam was used as the absorbent material. FIG. 7 shows an enlarged view of the thus-obtained wound dressing, taken from the perforated material side thereof. Also as in FIG. 7, it is known that the silicone resin clung and adhered to a part of the polyurethane foam of the absorbent material.

Comparative Example 1

A wound dressing was produced according to the same method as in Example 1, for which, however, the silicone resin was applied only to the bottom face of the perforated material. Accordingly, in the wound dressing of Comparative Example 1, the part of the absorbent material facing the through-holes of the perforated material is not coated with the silicone resin. FIG. 8 shows an enlarged view of the thus-obtained wound dressing, taken from the perforated material side thereof.

The test results in Examples and Comparative Example are shown in Table 1.

TABLE 1

| | | Example 1 | Example 2 | Comparative Example 1 |
|---|---|---|---|---|
| Perforated Material | Average through-holes cross section ($mm^2$) | 0.98 | 0.98 | 0.98 |
| | Perforated rate (%) | 34 | 34 | 34 |
| | Thickness (mm) | 0.32 | 0.32 | 0.32 |
| Absorbent material | Silicone resin coating amount ($g/m^2$) | 79 | 44 | 0 |
| Wound Dressing | Silicone resin coating amount ($g/m^2$) | 200 | 202 | 142 |
| | Adhesion (N/25 mm) | 0.25 | 0.96 | 0.33 |

The wound dressings obtained in Example 1 and Comparative Example 1 were tested for the possibility of enhancing the non-adhesiveness to a body tissue owing to coating the part of the absorbent material facing the through-holes of the perforated material with a silicone resin, according to the following evaluation.

[Evaluation of Non-Adhesiveness]

A 6-week age male SD rat is operated on to have a total skin defect having a diameter of 3 cm on the left abdomen. A sterilized wound dressing is applied to the wound, and fixed thereon by winding an elastic bandage around it. On day 2 and day 9 after the wounding, the wound dressing was peeled from the wound and checked for the adhesiveness thereof.

Results in Comparative Example 1

On day 2, the wound dressing obtained in Comparative Example 1 did not adhere to the wound on the silicone resin-coated face of the perforated material thereof, but adhered slightly thereto on the part of the through-holes of the perforated material. The wound surface from which the wound dressing had been peeled away was checked. As a result, the wound surface looked roughened along the profile of the perforated material.

The result may be because the tunica dartos tissue of the wound area of the SD rat would have invaded and adhered to the absorbent material through the through-holes of the perforated material. On day 9, the wound dressing adhered more firmly to the wound at the part of the through-holes of the perforated material thereof. When the wound dressing was peeled away from the wound surface, then much bleeding was seen from the wound surface. The result may be because, like on day 2, the neogenetic granulation tissue would have invaded and adhered to the wound tissue through the through-holes thereof after having taken the fibers of the absorbent material thereinto. The results are shown in FIG. 9.

Results in Example 1

On the other hand, the wound dressing in Example 1 did not adhere at all and could be peeled away on day 2. The wound surface from which the wound dressing had been peeled away was not roughened at all. On day 9, the wound dressing adhered lightly at the part of the through-holes of the perforated material, but little bleeding was seen from the wound surface from which the wound dressing had been peeled away. The difference in the constitution between Example 1 and Comparative Example 1 is that the part of the absorbent material facing the through-holes of the perforated material was partly coated with a silicone resin in the former. Accordingly, it has been confirmed that the present invention is effective for solving the problem of adhering of wound dressings to the tunica dartos and the granulation tissue of a wound. The results are shown in FIG. 10.

The invention claimed is:

1. A wound dressing comprising a perforated material having a top face and a bottom face and having plural through-holes, and an absorbent material disposed on the top face of the perforated material;
    wherein at least the bottom face of the perforated material is coated with an adhesive resin except leaving at least a part of the through-holes so as not to block up all the through-holes,
    at least a part of the absorbent material facing the through-holes of the perforated material is coated with the adhesive resin,
    the adhesive resin having adhesiveness to such a degree that, when the wound dressing of the invention is applied to a wound area and is removed from the wound area, then the wound dressing does not much irritate or damage skin and the wound,
    the adhesive resin penetrates from the bottom face of the perforated material into an inside thereof so as to reach the top face of the perforated material,
    and allowing fluid penetration from the bottom face side of the perforated material into an inside of the absorbent material.

2. A wound dressing comprising a perforated material having a top face and a bottom face and having plural through-holes, and an absorbent material disposed on the top face of the perforated material;
    wherein the top face and the bottom face of the perforated material are coated with an adhesive resin except leaving at least a part of the through-holes so as not to block up all the through-holes, at least a part of the absorbent material facing the through-holes of the perforated material is coated with the adhesive resin, the perforated material and the absorbent material are adhered to each other with the adhesive resin overlying the top face of the perforated material, the adhesive resin having adhesiveness to such a degree that, when the wound dressing of the invention is applied to a wound area and is removed from the wound area, then the wound dressing does not much irritate or damage skin and the wound, the adhesive resin penetrates from the bottom face of the perforated material into an inside thereof so as to reach the top face of the perforated material, and allowing fluid penetration from the bottom face side of the perforated material into the inside of the absorbent material.

3. The wound dressing according to claim 1, wherein the adhesive resin is a silicone resin.

4. The wound dressing according to claim 1, wherein the adhesive resin is an adhesive gel.

5. The wound dressing according to claim 1, wherein the part of the absorbent material facing the through-holes of the perforated material is coated with the adhesive resin in such a degree that the coating does not interfere with fluid penetration from the bottom face side of the perforated material into the inside of the absorbent material.

6. The wound dressing according to claim 1, wherein nearly the entire bottom face of the perforated material is coated with the adhesive resin except leaving almost all the through-holes so as not to block up almost all the through-holes, and the part of the absorbent material that faces almost all the through-holes of the perforated material is coated with the adhesive resin.

7. The wound dressing according to claim 1, wherein the perforated material has an average through-holes cross section of from 0.01 to 10 mm$^2$ and a perforated rate of from 5 to 70%.

8. A method for producing a wound dressing which comprises a perforated material having a top face and a bottom face and having plural through-holes, and an absorbent material disposed on the top face of the perforated material, and in which at least the bottom face of the perforated material is coated with an adhesive resin except leaving at least a part of the through-holes so as not to block up all the through-holes, and at least a part of the absorbent material facing the through-holes of the perforated material is coated with the adhesive resin, and to allow fluid penetration from the bottom face side of the perforated material into the inside of the absorbent material, the method comprising the following steps:

(P1) a step of applying a adhesive resin to a release sheet, (P2) a step of putting a perforated material on the coated face of the adhesive resin before curing and putting an absorbent material on the top face of the perforated material to thereby coat the perforated material and the absorbent material with the adhesive resin, (P3) a step of heating and curing the adhesive resin.

9. A method for producing a wound dressing which comprises a perforated material having a top face and a bottom face and having plural through-holes, and an absorbent material disposed on the top face of the perforated material, and in which the top face and the bottom face of the perforated material are coated with an adhesive resin except leaving at least a part of the through-holes so as not to block up all the through-holes, and at least a part of the absorbent material facing the through-holes of the perforated material is coated with the adhesive resin, and the perforated material and the absorbent material are adhered to each other with the adhesive resin overlying the top face of the perforated material, and to allow fluid penetration from the bottom face side of the perforated material into the inside of the absorbent material, the method comprising the following steps:

(P1) a step of applying a adhesive resin to a release sheet, (P2A) a step of putting a perforated material on the coated face of the adhesive resin before curing and putting an absorbent material on the top face of the perforated material, and to make the adhesive resin penetrate from the bottom face of the perforated material into the inside thereof so as to reach the top face of the perforated material, whereby the perforated material and the absorbent material are adhered to each other with the low-adhesive resin, and the perforated material and the absorbent material are coated with the adhesive resin, (P3) a step of heating and curing the adhesive resin.

10. The method for producing a wound dressing according to claim 8, wherein the adhesive resin is a silicone resin.

11. The wound dressing according to claim 2, wherein the adhesive resin is a silicone resin.

12. The wound dressing according to claim 2, wherein the adhesive resin is an adhesive gel.

13. The wound dressing according to claim 2, wherein the part of the absorbent material facing the through-holes of the perforated material is coated with the adhesive resin in such a degree that the coating does not interfere with fluid penetration from the bottom face side of the perforated material into the inside of the absorbent material.

14. The wound dressing according to claim 3, wherein the part of the absorbent material facing the through-holes of the perforated material is coated with the adhesive resin in such a degree that the coating does not interfere with fluid penetration from the bottom face side of the perforated material into the inside of the absorbent material.

15. The wound dressing according to claim 4, wherein the part of the absorbent material facing the through-holes of the perforated material is coated with the adhesive resin in such a degree that the coating does not interfere with fluid penetration from the bottom face side of the perforated material into the inside of the absorbent material.

* * * * *